(12) United States Patent
Touzan et al.

(10) Patent No.: US 6,281,203 B1
(45) Date of Patent: Aug. 28, 2001

(54) COSMETIC AND/OR DERMATOLOGICAL COMPOSITION CONTAINING SALICYCLIC ACID DERIVATIVE AND ITS USE

(75) Inventors: Philippe Touzan, Paris; Patricia Delambre, Ablon-sur-Seine, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/375,488

(22) Filed: Aug. 17, 1999

(30) Foreign Application Priority Data

Aug. 17, 1998 (FR) .................................. 98 10472

(51) Int. Cl.[7] .............................. A61K 31/60; A61K 7/00
(52) U.S. Cl. ............................. 514/159; 424/401
(58) Field of Search ................... 514/568, 159; 424/62, 401

(56) References Cited

U.S. PATENT DOCUMENTS

| | | | |
|---|---|---|---|
| 4,720,353 | * | 1/1988 | Bell ...................................... 252/309 |
| 5,531,993 | | 7/1996 | Griat . |
| 5,653,970 | * | 8/1997 | Vermeer ............................ 424/70.24 |
| 5,665,364 | * | 9/1997 | McAtee et al. ....................... 424/401 |
| 5,723,109 | * | 3/1998 | Causse et al. ......................... 424/62 |
| 5,811,111 | * | 9/1998 | McAtee et al. ....................... 424/401 |

FOREIGN PATENT DOCUMENTS

| | | |
|---|---|---|
| 0 378 936 A | 7/1990 | (EP) . |
| 2 755 366 A | 5/1998 | (FR) . |
| WO 97/44049 | 11/1997 | (WO) . |
| WO 98/10741 | 3/1998 | (WO) . |
| WO 98/22083 | 5/1998 | (WO) . |

OTHER PUBLICATIONS

Database Registry, Glucanate . . . , Abstract. from CA Registry/STN.*

* cited by examiner

Primary Examiner—William R. A. Jarvis
Assistant Examiner—Vickie Kim
(74) Attorney, Agent, or Firm—Oblon, Spivak, McClelland, Maier & Neustadt, P.C.

(57) ABSTRACT

A cosmetic and/or dermatological composition, which contains (i) salicylic acid and/or at least one salicylic acid derivative, (ii) at least one ester of a fatty acid and glucose and/or alkylglucose, and (iii) at least one oxyethylenated ether of a fatty acid ester of glucose and/or alkylglucose. The composition allows a gentle treatment of the human skin. The composition is useful for treating the effects of skin ageing, and treating skin disorders such as acne.

21 Claims, No Drawings

COSMETIC AND/OR DERMATOLOGICAL COMPOSITION CONTAINING SALICYCLIC ACID DERIVATIVE AND ITS USE

BACKGROUND OF THE INVENTION

1. Field of the Invention

The invention relates to a cosmetic and/or dermatological composition and to the use of this composition for combating ageing of the skin, and for treating skin disorders.

2. Discussion of the Background

Beta-hydroxy acids and in particular, salicylic acid and its derivatives, have been known as keratolytic agents for treating acne and as antiageing agents in cosmetic and/or dermatological compositions. Thus, document WO-A-93/10756 describes the use of a composition based on salicylic acid for treating wrinkles and the documents FR-A-2,581,542 and EP-A-378,936 describe the use of salicylic acid derivatives for treating acne and the signs of ageing.

Salicylic acid and its derivatives are of great interest given their biological effects on the skin, particularly in treating the principal clinical signs of skin ageing which are fine lines and wrinkles, the disorganization of the "grain" of the skin, the modification of the complexion of the skin and the loss of skin firmness and tone. Salicylic acid derivatives have a higher keratolytic activity and effective bacteriostatic activity compared to salicylic acid.

Unfortunately, the use of these agents can cause prickling, itching and pulling after their application, which can lead to great discomfort. Therefore, the use of these compounds for treating persons with sensitive skin is not recommended.

Consequently, the need remains for a cosmetic and/or dermatological composition based on such compounds, which does not exhibit the disadvantages of the prior art.

SUMMARY OF THE INVENTION

It is an object of this invention to prepare compositions for treating skin to combat the effects of ageing.

It is another object of the invention to prepare compositions suitable for treating skin disorders.

It is another object of the invention to devise a process for treating the human body for cosmetic and dermatological purposes.

The applicant has found, unexpectedly, that the tolerance of individuals to salicylic acid and its derivatives can be increased by incorporating them into an oil-in-water (O/W) emulsion containing a mixture of at least one fatty ester of glucose or an alkylglucose and at least one oxyalkylenated ether of a fatty ester of glucose or an alkylglucose.

The present invention is directed to a cosmetic and/or dermatological composition in the form of an oil-in-water emulsion, which contains (i) salicylic acid and/or at least one salicylic acid derivative, (ii) at least one ester of a fatty acid and glucose and/or an alkylglucose, and (iii) at least one oxyalkylenated ether of a fatty acid ester of glucose and/or an alkylglucose.

The combination of a fatty acid ester of (alkyl)glucose and an oxyalkylenated ether of a fatty acid ester of (alkyl) glucose unexpectedly provides a composition which is perfectly tolerated when applied to the face or skin of the human body.

DESCRIPTION OF THE PREFERRED EMBODIMENTS OF THE INVENTION

The fatty chain in the ester of a fatty acid and an (alkyl)glucose and in the oxyalkylenated ether of a fatty acid ester of an (alkyl)glucose may contain from about 8 to about 30 carbon atoms and more particularly from about 10 to about 22 carbon atoms.

Suitable esters of a fatty acid and glucose or an alkylglucose, include the fatty esters of methylglucoside such as the diester of methylglucoside and oleic acid (CTFA name: methyl glucose dioleate); the mixed ester of methylglucoside and an oleic acid/hydroxystearic acid mixture (CTFA name: methyl glucose dioleate/hydroxystearate); the ester of methylglucoside and isostearic acid (CTFA name: methyl glucose isostearate); the ester of methylglucoside and lauric acid (CTFA name: methyl glucose laurate); the ester of methylglucoside and isostearic acid (CTFA name: methyl glucose isostearate); a mixture of the monoester and diester of methylglucoside and isostearic acid (CTFA name: methyl glucose sesquiisostearate); a mixture of the monoester and diester of methylglucoside and stearic acid (CTFA name: methyl glucose sesquistearate) and a product marketed under the name Glucate SS by the company Amerchol. Mixtures of these esters are also contemplated.

Preferably, the ester of a fatty acid and glucose or alkylglucose is introduced into the oily phase of the emulsion and in a quantity sufficient to achieve the desired result. This amount may range from about 0.1% to about 10% by weight, preferably from about 1% to about 3% by weight relative to the total weight of the composition.

The oxyalkylenated ether of a fatty acid and glucose or alkylglucose may contain from about 10 to about 100 oxyalkylenated groups (or moles of an alkylene oxide such as ethylene oxide, propylene oxide or mixtures thereof), preferably from about 20 to about 40 oxyalkylenated groups. Suitable ethers of a fatty acid and glucose or alkylglucose, include, for example, oxyethylenated ethers of a fatty acid and methylglucose, such as a polyethylene glycol ether of a diester of methylglucose and stearic acid containing about 20 moles of ethylene oxide (CTFA name: PEG-20 methyl glucose distearate marketed under the name Glucam E-20 distearate by the company Amerchol); a polyethylene glycol ether of a mixture of the monoester and diester of methylglucose and stearic acid containing about 20 moles of ethylene oxide (CTFA name: PEG-20 methyl glucose sesquistearate marketed under the name Glucamate SSE-20 by the company Amerchol and under the name Grillocose PSE-20 by the company Goldschmidt). Mixtures of these oxyalkylenated ethers can be used.

Preferably, the oxyalkylenated ether is introduced into the aqueous phase of the emulsion and in a quantity sufficient to achieve the desired result. The oxyalkylenated ether may be used in an amount of from about 0.1% to about 10% by weight, preferably from about 1% to about 3% by weight relative to the total weight of the composition.

The compositions of the invention also contain salicylic acid and/or one or more salicylic acid derivatives. Suitable salicylic acid derivatives include those of formula (I) or a salt thereof:

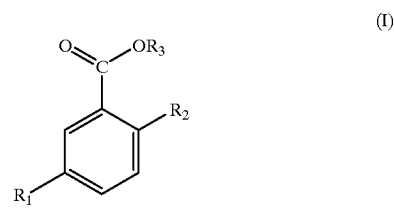

in which:
R$_1$ represents hydrogen or a saturated, linear, branched or cyclized aliphatic hydrocarbon group or an alkoxy, ester or ketoxy group, or an unsaturated group having at least one conjugated or unconjugated double bond, wherein these groups may contain from 1 to about 22 carbon atoms and may be substituted with at least one substituent chosen from halogen atoms, the trifluoromethyl group, hydroxyl groups in a free form or esterified by an acid having from 1 to about 6 carbon atoms or a carboxyl group, which is free or esterified by a lower alcohol having from 1 to about 6 carbon atoms;

R$_2$ represents a hydroxyl group or an ester of formula (II):

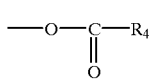
(II)

where R$_4$ represents a saturated aliphatic group or an alkenyl group having from 1 to about 18 carbon atoms;

R$_3$ represents hydrogen or a saturated or unsaturated linear or branched chain having from 2 to about 30 carbon atoms, optionally containing one or more substituents such as those listed above. Alkyl and alkenyl radicals containing from 2 to about 30 carbon atoms are suitable and are optionally substituted. The preferred substituent is a hydroxyl radical.

When R$_3$ is hydrogen, one can use salts of the compounds of formula (I), particularly salts obtained by reaction with a base. Suitable bases include alkali metal hydroxides (sodium and potassium hydroxides), ammonium hydroxide, organic bases such as primary, secondary, tertiary or cyclic organic amines, and amino acids. Specific examples of bases include glycine, lysine, arginine, taurine, histidine, alanine, valine, cysteine, trihydroxymethylaminomethane (TRISTA) and triethanolamine.

According to a preferred embodiment of the invention, compositions are prepared using derivatives of formula (I) where R$_1$ contains at least 4 carbon atoms. For example, R$_1$ may be a saturated linear alkyl or alkoxy radical having from 4 to 11 carbon atoms.

Derivatives of formula (I) in which R$_2$ is hydroxyl and R$_3$ is hydrogen, include 5-n-octanoylsalicylic acid (CTFA name: Capryloyl Salicylic Acid), 5-n-decanoylsalicylic acid, 5-n-dodecanoylsalicylic acid, 5-n-octylsalicylic acid, 5-n-heptyloxysalicylic acid, 5-tert-octylsalicylic acid, 5-butoxysalicylic acid, 5-ethoxysalicylic acid, 5-methoxysalicylic acid, 5-propoxysalicylic acid, 5-methylsalicylic acid, 5-ethylsalicylic acid and 5-propylsalicylic acid, optionally treated with a base.

When R$_1$ represents hydrogen and R$_2$ a hydroxyl group, the derivative of formula (I) is a salicylic acid ester. Preferred compounds include esters of fatty alcohols such as dodecyl, hexadecyl, stearyl, cetyl, myristyl, linoleyl, octyl, oleyl and tridecyl alcohols, or esters of butyl, propyl and ethyl alcohols, or esters of polyols such as propylene glycol, butylene glycol, ethylene glycol or glycerol, or mixtures of these esters. Specific examples include cetyl salicylate, dodecyl salicylate and tridecyl salicylate. Salicylic acid and its derivatives are used in the compositions of the present invention in an amount sufficient to achieve the desired cosmetic or dermatological result. The quantity of salicylic acid and/or salicylic acid derivatives ranges from about 0.001 to about 10% by weight, preferably from about 0.05 to about 5% by weight relative to the total weight of the composition.

According to a preferred embodiment of the invention, the composition has a pH close to that of the skin and preferably ranges from about 4 to about 7. This results in a high compatibility between the emulsion of the invention and the skin.

The compositions of the invention are intended for topical application and appropriately include a physiologically acceptable medium. Physiologically acceptable medium is understood to mean a medium compatible with the skin, the mucous membranes (including the inside of the eyelids and the lips), the nails and/or the keratinous fibers (hair and eyelashes).

The oily phase of the present compositions may comprise the fatty acids and oils conventionally used in the cosmetic and/or dermatological fields. Suitable oils which can be used in the emulsions of the invention include oils of plant origin Oojoba, avocado, sesame, sunflower, maize, soyabean, safflower, grape seeds), mineral oils (petroleum jelly, optionally hydrogenated isoparaffins), synthetic oils (isopropyl myristate, cetearyl octanoate, polyisobutylene, ethylhexyl palmitate, alkyl benzoates), silicone oils (cyclomethicones such as cyclohexadimethylsiloxane, polydimethylsiloxanes, polymethylphenylsiloxanes, polydimethylfluorosiloxanes) and fluorinated oils. Other fatty substances which may be present in the oily phase include fatty acids, fatty alcohols such as stearyl alcohol, and waxes.

The oily phase of the emulsion may represent from about 1 to about 50% and preferably from about 5 to about 40% by weight relative to the total weight of the composition.

The aqueous phase of the emulsion may contain one or more alcohols and/or polyols such as ethanol, glycerin, butylene glycol, isoprene glycol, propylene glycol and sorbitol, in concentrations ranging from about 1 to about 20% by weight of the total weight of the composition. The aqueous phase generally represents from about 1 to about 80% and preferably from about 30 to about 70% by weight relative to the total weight of the composition.

The compositions of the invention may contain adjuvants which are customarily used in the cosmetic and/or dermatological fields. These include hydrophilic or lipophilic active agents, preservatives, antioxidants, perfumes, fillers, coloring matter (pigments or colorants), sunscreens, solvents and lipid vesicles. These adjuvants are normally present in amounts ranging from about 0.01 to about 20% of the total weight of the emulsion, and, depending on their nature, may be introduced into the aqueous phase or the oily phase of the composition, or alternatively into vesicles.

Suitable sunscreens include octocrylene (Uvinul N539 marketed by the company BASF), octyl methoxycinnamate (Parsol MCX marketed by the company Givaudan-Roure), and butyl methoxy-dibenzoylmethane (Parsol 1789 marketed by the company Givaudan-Roure).

Suitable solvents which may be used in the compositions of the invention include octyldodecanol.

Gelling agents may be employed to achieve the desired fluidity of the composition. Suitable gelling agents include clays, polysaccharide gums and their derivatives (xanthan gum, carboxymethylcellulose, hydroxypropyl guar), carboxyvinyl polymers or carbomers, polyacrylamides such as those marketed under the name SEPIGEL 305 by the company SEPPIC and at least partially crosslinked polymers of acrylamidomethylpropanesulphonic acid such as the product marketed under the name HOSTACERIN AMPS by the company HOECHST. These gelling agents are generally used at concentrations ranging from about 0.1 to about 10%, preferably about 0.1 to about 5% and most preferably from about 0.1 to about 3% of the total weight of the composition.

The compositions of the invention find application in dermatological treatments for the skin, the mucous membranes and/or the hair, including the scalp, and in particular, the protection, care and cleansing of, and/or as make-up for the skin and/or the mucous membranes, for the protection and/or care of the hair and/or for therapeutic treatment of the skin, the hair and/or the mucous membranes and more particularly the lips.

The compositions of the invention can be used in preparing care or cleansing products for the face, particularly in the form of lotions, creams or milks, and as make-up products (skin and lips) by incorporation of fillers, pigments or colorants. The compositions can be used to protect the skin from exposure to the sun by incorporation of sunscreen(s).

The compositions of the invention are appropriate for use in the care of the skin and/or the mucous membranes and/or the keratinous fibers of a human being. In particular, the compositions are suitable for combating the signs of skin ageing, for making the skin of the face and body smooth, for treating the wrinkles and fine lines of the skin, for stimulating the process of epidermal renewal and for treating acne and other skin disorders.

Skin disorders include zona, burns, eczema, demodicidosis, skin ulcer, fibrosis, control of cicatrizations, psoriasis, pruritus, dermatitis, ichthyosis, corns and verrucae.

The invention also provides a method for the protection, care and cleansing of the skin and mucous membranes and keratinous fibers of the human body by applying thereto compositions as defined above.

The invention also provides a method for combating the signs of skin ageing, for enhancing the brightness of ones complexion, for making the skin of the face and body smooth, for treating wrinkles and fine lines of the skin and for stimulating the process of epidermal renewal by applying to the skin a composition as defined above.

Other characteristics and advantages of the invention will emerge more clearly from the following examples which are given by way of illustration only and are not intended to limit the invention. The proportions are given in percentage by weight.

EXAMPLE 1
Cream

| | | |
|---|---|---|
| A | Glucate SS [Amerchol] (Methyl Glucose Sesquistearate) | 2% |
| | Steary1 alcohol | 1.5% |
| | Cyclomethicone | 10% |
| | Hydrogenated isoparaffin | 7% |
| | Octocrylene (Uvinul N539) | 2% |
| | Octyldodecanol | 5% |
| | Capryloyl Salicylic Acid | 1% |
| | Perfume | 0.3% |
| B | Water qs | 100% |
| | Glycerin | 5% |
| | Glucamate SSE-20 [Amerchol] (PEG-20 Methyl Glucose Sesquistearate) | 2% |
| | Preservatives | 0.6% |
| C | Hostacerin AMPS | 1.2% |
| D | Sepigel 305 | 1% |

Procedure:

Phase A and phase B are each heated at 75° C. until solubilization.

A is introduced into B, with stirring, until a fine and uniform emulsion is obtained.

Compound C is added at 60° C. and dispersed with stirring, and then compound D is introduced in the same manner. The mixture is cooled, with stirring.

The cream obtained, when applied to the skin, enhances brightness of the complexion.

EXAMPLE 2
Fluid emulsion

| | | |
|---|---|---|
| A | Glucate SS [Amerchol](Methyl Glucose Sesquistearate) | 1.5% |
| | Stearyl alcohol | 1% |
| | Cyclomethicone | 5% |
| | Octocrylene (Uvinul N539) | 2% |
| | Octyldodecanol | 3% |
| | Capryloyl Salicylic Acid | 5% |
| | Perfume | 0.2% |
| | Preservatives | 0.1% |
| B | Water qs | 160% |
| | Glycerin | 3% |
| | Glucamate SSE-20 [Amerchol] (PEG-20 Methyl Glucose Sesquistearate) | 1.5% |
| | Preservatives | 0.5% |
| C | Water | 15% |
| | Xantham gum | 0.1% |
| D | Sepigel 305 | 1% |

Procedure:

Phase A at 75° C. is introduced into phase B at 75° C., with stirring, until a fine and uniform emulsion is obtained.

Phase C is homogenized, with stirring, in water at 50° C. and then introduced, with stirring at 50° C., into the A+B mixture.

Compound D is introduced at 50° C. and dispersed, with stirring.

The fluid obtained is cooled, with stirring.

An emulsion is obtained which, upon regular application to the skin, enhances cellular renewal thereof.

TEST:

A test of cell viability on reconstructed skin (EPISKIN TM) was carried out with a carrier which is an emulsified gel based on hostacerin AMPS (comparative) and with an emulsion according to the invention. The higher the cell viability, the better the tolerance. The cell viability results are given in the following table:

| | Emulsified gel carrier | | | Glucate/ glucamate emulsion | | |
|---|---|---|---|---|---|---|
| % Capryloyl salicylic acid | 0.1 | 0.3 | 0.5 | 0.1 | 0.3 | 0.5 |
| Cell viability performed on EPISKIN ™ | 88.4% | 67.7% | 34.4% | 100% | 100% | 78.9% |

This test shows that the emulsion according to the invention significantly increase the tolerance of salicylic acid derivatives.

The present application is based on French Application No. 9810472, filed Aug. 17, 1998, the entire contents of which are incorporated herein by reference.

What is claimed is:

1. A composition comprising an oil-in water emulsion containing:
(i) at least one compound selected from salicylic acid or a salicylic acid derivative, (ii) at least one compound selected from fatty acid esters of glucose or fatty acid esters of an alkylglucose, and (iii) at least one compound selected from an oxyalkylenated ether of either a fatty acid ester of glucose or a fatty acid ester of an alkylglucose, wherein said oxyalkylenated ether is an oxyethylenated ether, and contains from about 10 to about 100 oxyethylenated groups, wherein said salicylic acid derivative is of a formula (I) or a salt thereof:

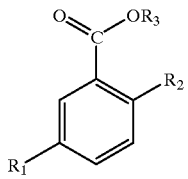

(I)

in which:

$R_1$ represents hydrogen or a saturated, linear, branched or cyclized aliphatic hydrocarbon group or an alkoxy, ester or ketoxy group, or an unsaturated group having at least one conjugated or unconjugated double bonds, wherein these groups contain from 1 to about 22 carbon atoms and optionally are substituted with at least one substituent chosen from halogen atoms, the trifluoromethyl group, the hydroxyl groups in a free form or esterified by an acid having from 1 to about 6 carbon atoms or a carboxyl group, which is free or esterified by a lower alcohol having from 1 to about 6 carbon atoms;

$R_2$ represents a hydroxyl group or an ester of formula (II):

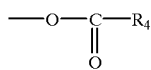

(II)

where $R_4$ represents a saturated aliphatic group or an alkenyl group having from 1 to about 18 carbon atoms;

$R_3$ represents hydrogen or a saturated or unsaturated linear or branched chain having from 2 to about 30 carbon atoms, optionally containing one or more substituents as defined above;

and wherein the pH of the composition is from 4 to 7.

2. A composition according to claim 1, wherein the fatty acid chain in said fatty acid esters of glucose or (alkyl)glucose contains from about 8 to about 30 carbon atoms.

3. A composition according to claim 1, wherein the said ester of glucose or alkylglucose is at least one fatty ester of methylglucoside.

4. A composition according to claim 3, wherein the fatty ester of methylglucoside is chosen from the group consisting of a diester of methylglucoside and of oleic acid; a mixed ester of methylglucoside and an oleic acid/hydroxystearic acid mixture; an ester of methylglucoside and isostearic acid; an ester of methylglucoside and lauric acid; an ester of methylglucoside and isostearic acid; a mixture of a monoester and diester of methylglucoside and isostearic acid; a mixture of a monoester and diester of methylglucoside and stearic acid and mixtures thereof.

5. A composition according to claim 1, wherein the amount of fatty acid ester of glucose or alkylglucose ranges from about 0.1% to about 10%.

6. A composition according to claim 1, wherein the oxyalkylenated ether of a fatty acid ester of glucose or alkylglucose is chosen from the oxyethylenated ethers of fatty acid esters of methylglucose.

7. A composition according to claim 1, wherein the oxyalkylenated ether of a fatty acid ester of glucose or alkylglucose is chosen from the group consisting of a polyethylene glycol ether of a diester of methylglucose and stearic acid containing about 20 moles of ethylene oxide, the polyethylene glycol ether of a mixture of the monoester and diester of methylglucose and stearic acid containing about 20 moles of ethylene oxide, and mixtures thereof.

8. A composition according to claim 1, wherein the quantity of oxyalkylenated ether(s) of a fatty acid ester of (alkyl)glucose ranges from about 0.1% to about 10% by weight.

9. A composition according to claim 1, wherein the salicylic acid derivative is chosen from the group consisting of 5-n-octanoylsalicylic acid, 5-n-decanoylsalicylic acid, 5-n-dodecanoylsalicylic acid, 5-n-octylsalicylic acid, 5-n-heptyloxysalicylic acid, 5-tert-octylsalicylic acid, 5-butoxysalicylic acid, 5-ethoxysalicylic acid, 5-methoxysalicylic acid, 5-propoxysalicylic acid, 5-methylsalicylic acid, 5-ethylsalicylic acid, 5-propylsalicylic acid, the salts of these acids, cetyl salicylate, dodecyl salicylate, tridecyl salicylate and mixtures thereof.

10. A composition according to claim 1, wherein the quantity of salicylic acid or salicylic acid derivative(s) ranges from about 0.001 to about 10% by weight relative to the total weight of the composition.

11. A composition according to claim 1, wherein the oily phase represents from about 1 to about 50% by weight relative to the total weight of the composition.

12. A composition according to claim 1, which contains at least one gelling agent.

13. A composition according to claim 12, wherein the gelling agent is chosen from xanthan gum, polyacrylamides, at least partially crosslinked polymers of acrylamidomethylpropanesulphonic acid or mixtures thereof.

14. A method for the protection, care and cleansing of the skin, mucous membranes and keratinous fibers, which comprises applying thereto a composition according to claim 1.

15. A method for combating the signs of skin ageing, for enhancing the brightness of the complexion, for making the skin of the face and the body smooth, for treating the wrinkles and fine lines of the skin and stimulating the process of epidermal renewal, which comprises applying to the skin a composition according to claim 1.

16. A method for treating skin disorders which comprises applying to the skin a composition according to claim 1.

17. A composition according to claim 2, wherein said fatty acid chain contains from about 10 to about 22 carbon atoms.

18. A composition according to claim 5, wherein the amount of said fatty acid ester ranges from about 1% to about 3%.

19. A composition according to claim 1, wherein the ether contains from about 20 to about 40 oxyethylenated groups.

20. A composition according to claim 8, wherein the amount of said ether ranges from about 1% to about 3%.

21. A composition according to claim 10, wherein the amount of said acid or derivative ranges from about 0.05% to about 5%.

* * * * *

UNITED STATES PATENT AND TRADEMARK OFFICE
CERTIFICATE OF CORRECTION

PATENT NO. : 6,281,203 B1
DATED : August 28, 2001
INVENTOR(S) : Touzan et al.

It is certified that error appears in the above-identified patent and that said Letters Patent is hereby corrected as shown below:

<u>Column 8,</u>
Line 55, "A composition according to claim 1, wherein the..." should read
-- A composition according to claim 1, wherein said... --
Line 56, "contains from about 20 to 40 oxyethylenated groups...." should read
-- contains from about 20 to 40 oxyalkylated groups... --

Signed and Sealed this

Sixteenth Day of April, 2002

Attest:

JAMES E. ROGAN
*Attesting Officer*     *Director of the United States Patent and Trademark Office*